United States Patent
Peichel et al.

(10) Patent No.: US 12,102,817 B2
(45) Date of Patent: Oct. 1, 2024

(54) METHOD FOR DETERMINING COUPLING COEFFICIENT FOR WIRELESS POWER TRANSFER

(71) Applicant: Medtronic, Inc., Minneapolis, MN (US)

(72) Inventors: David J. Peichel, Minneapolis, MN (US); Can Cinbis, Salt Lake City, UT (US); Jonathan P. Roberts, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 933 days.

(21) Appl. No.: 17/097,375

(22) Filed: Nov. 13, 2020

(65) Prior Publication Data

US 2021/0170082 A1 Jun. 10, 2021

Related U.S. Application Data (60) Provisional application No. 62/945,926, filed on Dec. 10, 2019.

(51) Int. Cl.
*A61M 60/875* (2021.01)
*H01F 38/14* (2006.01)
(Continued)

(52) U.S. Cl.
CPC .......... *A61M 60/875* (2021.01); *H01F 38/14* (2013.01); *H02J 7/02* (2013.01); *H02J 50/12* (2016.02);
(Continued)

(58) Field of Classification Search
CPC .... A61M 2205/3507; A61M 2205/502; A61M 2205/52; A61M 2205/581;
(Continued)

(56) References Cited

U.S. PATENT DOCUMENTS

| 9,126,490 B2 | 9/2015 | Cook et al. |
| 9,948,112 B2 | 4/2018 | Hao et al. |
| 9,997,928 B2 | 6/2018 | Petersen et al. |
| 2007/0100395 A1* | 5/2007 | Ibrahim ............... A61B 5/4872 607/57 |

(Continued)

FOREIGN PATENT DOCUMENTS

| WO | 2017165410 A1 | 9/2017 |
| WO | 2018208992 A1 | 11/2018 |

OTHER PUBLICATIONS

International Search Report and Written Opinion dated Feb. 18, 2021, for corresponding International Application No. PCT/US2020/060715; International Filing Date: Nov. 16, 2020 consisting of 8—pages.

*Primary Examiner* — Christopher A Flory
(74) *Attorney, Agent, or Firm* — Shumaker & Sieffert, P.A.

(57) ABSTRACT

An external power source, implantable medical device, and method for indicating an extent of power transfer between an external coil to an internal coil associated with the implantable medical device. According to one aspect, a method includes determining a parameter that depends on an extent to which the external coil is aligned with the internal coil, where the parameter includes at least one of an indication of an internal coil output power and power transfer efficiency and a resonant frequency of the external coil when inductively coupled to the internal coil. The method further includes indicating an extent to which the external coil is aligned with the internal coil based on the parameter.

12 Claims, 6 Drawing Sheets

(51) Int. Cl.
*H02J 7/02* (2016.01)
*H02J 50/12* (2016.01)
*H02J 50/90* (2016.01)

(52) U.S. Cl.
CPC ...... *H02J 50/90* (2016.02); *A61M 2205/3507* (2013.01); *A61M 2205/502* (2013.01); *A61M 2205/52* (2013.01); *A61M 2205/581* (2013.01); *A61M 2205/583* (2013.01); *A61M 2205/587* (2013.01); *A61M 2205/8206* (2013.01); *A61M 2205/8243* (2013.01)

(58) Field of Classification Search
CPC .... A61M 2205/583; A61M 2205/8206; A61M 60/875; H02J 50/12; H02J 50/90
See application file for complete search history.

(56) References Cited

U.S. PATENT DOCUMENTS

| | | |
|---|---|---|
| 2012/0032522 A1 | 2/2012 | Schatz et al. |
| 2012/0146575 A1* | 6/2012 | Armstrong .......... A61M 60/178 320/108 |
| 2013/0241306 A1* | 9/2013 | Aber ........................ H01Q 7/00 307/104 |
| 2015/0094887 A1 | 4/2015 | Kawashima |
| 2016/0022889 A1* | 1/2016 | Bluvshtein .......... A61M 60/875 600/16 |
| 2016/0022891 A1* | 1/2016 | Bluvshtein .......... H02J 7/00304 600/16 |
| 2016/0254703 A1 | 9/2016 | Hansen |
| 2016/0336813 A1 | 11/2016 | Yeh et al. |
| 2018/0078329 A1* | 3/2018 | Hansen .................. H02J 50/10 |
| 2019/0009097 A1* | 1/2019 | Hartley .................. H02J 50/90 |
| 2019/0184159 A1* | 6/2019 | Yeh ..................... A61N 1/37252 |
| 2020/0155843 A1* | 5/2020 | Yeh ........................ H02J 50/20 |
| 2020/0306528 A1* | 10/2020 | Linden ............... A61N 1/36114 |

* cited by examiner

METHOD FOR DETERMINING COUPLING COEFFICIENT FOR WIRELESS POWER TRANSFER

CROSS-REFERENCE TO RELATED APPLICATION

This application is related to and claims priority to U.S. Provisional patent Application Ser. No. 62/945,926, filed Dec. 10, 2019, the entirety of which is incorporated herein by reference.

FIELD

The present technology is generally related to wireless power transfer for implantable medical devices and, more particularly, to indicating energy coupling between an external charging source coil and an internal coil associated with an internal rechargeable power source.

BACKGROUND

Implantable medical devices may be used to monitor a patient condition and/or deliver therapy to the patient. In long term or chronic uses, implantable medical devices may include a rechargeable power source (e.g., one or more capacitors or batteries) that extends the operational life of the implantable medical device to weeks, months, or even years over a non-rechargeable device.

Figure 1:
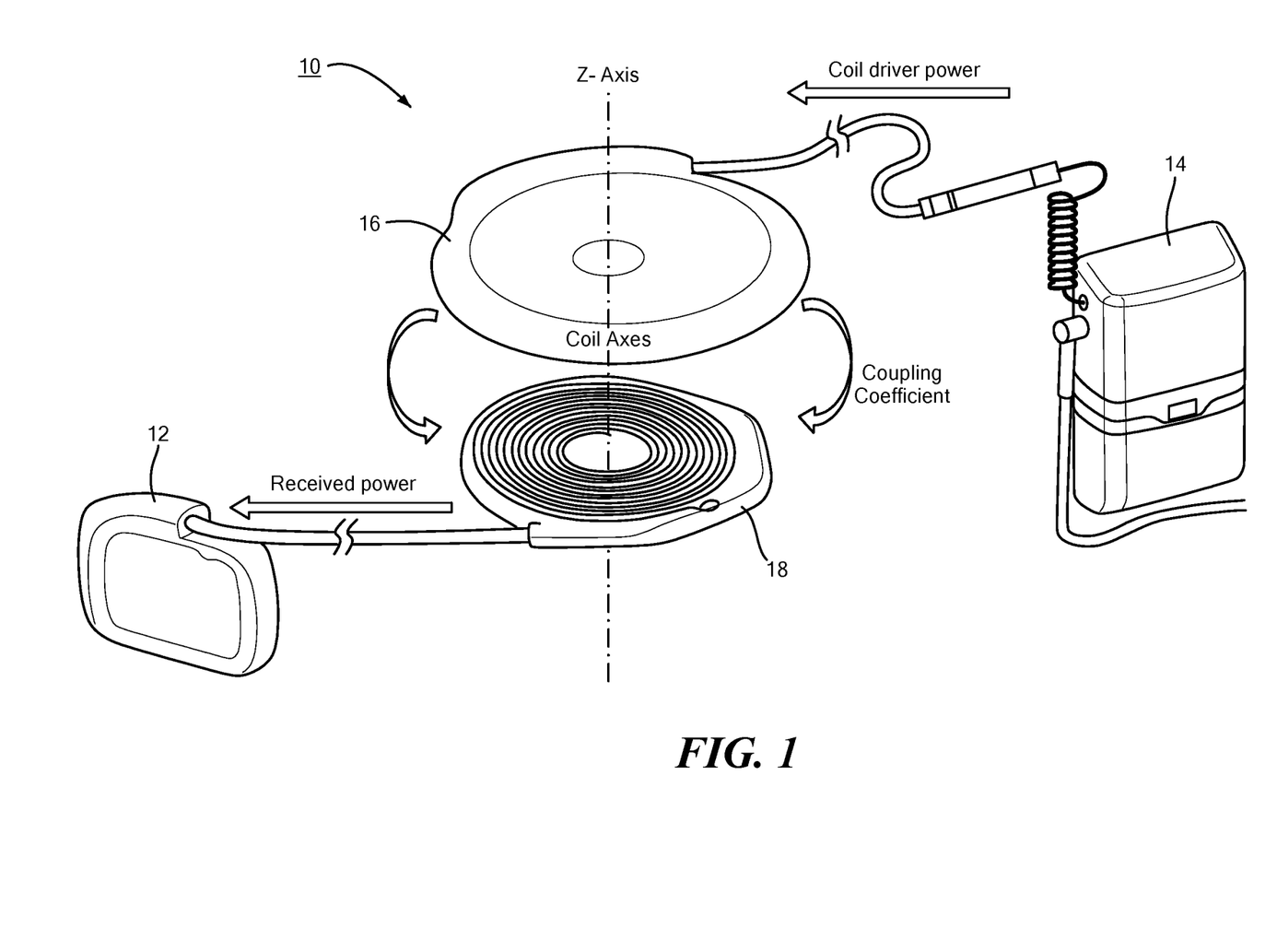
FIG. 1 is one example of an external charging device in inductive communication with an implantable medical device.

Referring to FIG. 1, when the energy stored in the rechargeable power source within the implantable medical device 12 has been depleted, the patient may use an external charging device 14 to recharge the rechargeable power source. Since the rechargeable power source is implanted in the patient and the charging device 14 is external to the patient, this charging process may be referred to as transcutaneous charging. In some examples, transcutaneous charging may be performed via inductive coupling between a primary, external coil 16 in the charging device and a secondary, internal coil 18 in the implantable medical device 12.

An electrical current applied to the primary coil 16 generates a magnetic field, and when the external coil 16 is aligned to the internal coil 18, the magnetic field induces an electrical current in the internal coil 18 within the patient. Charging circuitry within the implantable medical device 12 then applies current from the internal coil 18 to charge the rechargeable power source within the implantable medical device 12. The power coupled from the external coil to the internal coil may also be used to power a pump in some implantable medical devices. With transcutaneous transfer via inductive coils, the external charging device 14 does not need to physically connect with the rechargeable power source for charging to occur.

Note that as the two coils move closer to each other and/or their axes become more aligned, the coupling between the coils increases and less current in the primary (external) coil 16 is needed to transfer a given amount of power to the secondary (internal) coil 18. Conversely, as the coils move farther apart and become more misaligned, more current is needed in the external coil to transfer the given amount of power to the internal coil. Therefore, optimal wireless transfer of power from the external coil 16 of the external charging device 14 to the internal coil 16 of the internal rechargeable power source and avoidance of overheating of the external coil is achieved by aligning the internal and external coils when placed close together. The coils are aligned when their coil axes are substantially coincident, where the axis of a coil is perpendicular to the plane of the coil windings, as shown by the z-axis in FIG. 1. Since the user of the medical implant is ordinarily responsible for aligning the external coil with the internal coil to recharge the battery of the implanted device, the user should desirably know to what extent the coils are aligned.

SUMMARY

The techniques of this disclosure generally relate to indicating to a patient an extent of energy coupling between an external charging source coil and the internal coil associated with the internal rechargeable power source of an implanted medical device.

According to some embodiments, an end to end efficiency calculation is performed based on a transfer of an indication of an amount of power received at the internal coil back to the external charging source. The power indication returned from the internal medical implant device is used to determine a ratio of output power to input power as a measure of efficiency. This efficiency is correlated to a coupling coefficient which is used as an indicator of coil alignment.

According to some embodiments, a driving frequency applied to the external charging coil is adjusted to track the natural resonance frequency of the system. As the coupling coefficient increases between the two coils, the natural resonance frequency of the system will increase. Using a graph of operating frequency versus coupling coefficient, the coupling coefficient can be estimated and used to indicate an extent of alignment.

In one aspect, the present disclosure provides an external power source configured to supply power through inductive coupling of power from an external coil to an internal coil associated with an implanted medical device. The external power source includes a memory configured to store an internal coil output power, a determined efficiency, and a corresponding coupling coefficient. The external power source also includes a processor in communication with the memory. The processor is configured to receive an internal coil output power. The processor is also configured to determine an efficiency as the ratio of the internal coil output power to an amount of power applied to the external coil. The processor is also configured to determine a coupling coefficient based on the determined efficiency and generate an indication of an orientation of the external coil relative to the internal coil, the indication based at least in part on the determined coupling coefficient.

According to this aspect, in some embodiments, the indication of orientation is an audible tone that changes frequency as the orientation changes. In some embodiments, the determined coupling coefficient is determined from a look up table stored in the memory, the look up table providing a different coupling coefficient for each of a plurality of efficiency values and received power values. In some embodiments, the determined coupling coefficient is determined according to a formula that relates the determined efficiency to the determined coupling coefficient. In some embodiments, the indication includes a variable graphical indicator that varies according to an alignment of the external coil relative to the internal coil. In some embodiments, the indication varies as an angle between an axis of the external coil and an axis of the internal coil varies. In some embodiments, the indication varies as a distance between the external coil and the internal coil varies.

According to another aspect, an external power source is configured to supply power through inductive coupling of power from an external coil to an internal coil associated with an implanted medical device. The external power source includes a memory configured to store an internal coil output power, a determined efficiency, and a corresponding coupling coefficient. A processor is in communication with the memory. The processor is configured to apply a signal to the external coil, the signal having an applied operating frequency that matches a resonant frequency of the external coil coupled to the internal coil. The processor is further configured to determine a coupling coefficient based at least in part on the applied operating frequency and generate an indication indicative of an orientation of the external coil relative to the internal coil, the display based at least in part on the determined coupling coefficient.

According to this aspect, in some embodiments, the determined coupling coefficient is determined from a look up table stored in the memory, the look up table providing a different coupling coefficient for each of a plurality of operating frequencies. In some embodiments, the determined coupling coefficient is determined according to a formula that relates the applied operating frequency to the determined coupling coefficient. In some embodiments, the indication includes a variable graphical indicator that varies according to an alignment of the external coil relative to the internal coil. In some embodiments, the indication varies as an angle between the external coil and the internal coil varies. In some embodiments, the indication varies as a distance between the external coil and the internal coil varies.

According to yet another aspect, an implantable medical device includes a charging circuit configured to receive power from an internal coil and convert the received power to a charging current and a rechargeable battery configured to receive the charging current and charge in response to the charging current. The implantable medical device also includes a sampling circuit configured to determine a value indicative of a power that is input to the implantable medical device via the internal coil and transfer the determined value to an external power source.

According to this aspect, in some embodiments, the sampling circuit transfers the determined value to the external power source via the internal coil. In some embodiments, the sampling circuit transfers the determined value to the external power source via a wireless transmitter of the implantable medical device. In some embodiments, the determined value is a number on a scale known to the external power source.

According to yet another aspect, a method for indicating an extent of inductive coupling of power from an external coil to an internal coil associated with an implanted medical device is provided. The method includes determining a parameter that depends on an extent to which the external coil is aligned with and in proximity to the internal coil, the parameter being based at least in part on at least one of an input power applied to the external coil, an internal coil output power and a resonant frequency of the external coil when inductively coupled to the internal coil. The method also includes generating an indication of the extent to which the external coil is aligned with and in proximity to the internal coil based on the parameter. Note that in some embodiments, this method may be performed in a device that is physically separated from the external power source and the implantable medical device, the physically separated device being in wireless or wireline communication with at least one of the external power source and the implantable medical device.

According to this aspect, in some embodiments, the indication is an audible tone that varies as an orientation of the external coil varies with respect to an orientation of the internal coil. In some embodiments, the indication is an audible tone that is pulsed at a rate that is based on a relative alignment between the external coil and the internal coil. In some embodiments, the indication is communicated via at least one of a cell phone and a wrist worn device in wireless communication with at least one of an external power supply having the external coil and the implantable medical device.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, an implantable medical device or an external charging source.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

As used herein, the term "orientation," "alignment" or "misalignment" refers to the radial distance, axial distance and tilt or rotation between the axes of the two coils. The term "indicative of an orientation" means indicative of the radial/axial distance and/or the rotation/tilt between the axis of the two coils.

Figure 2:
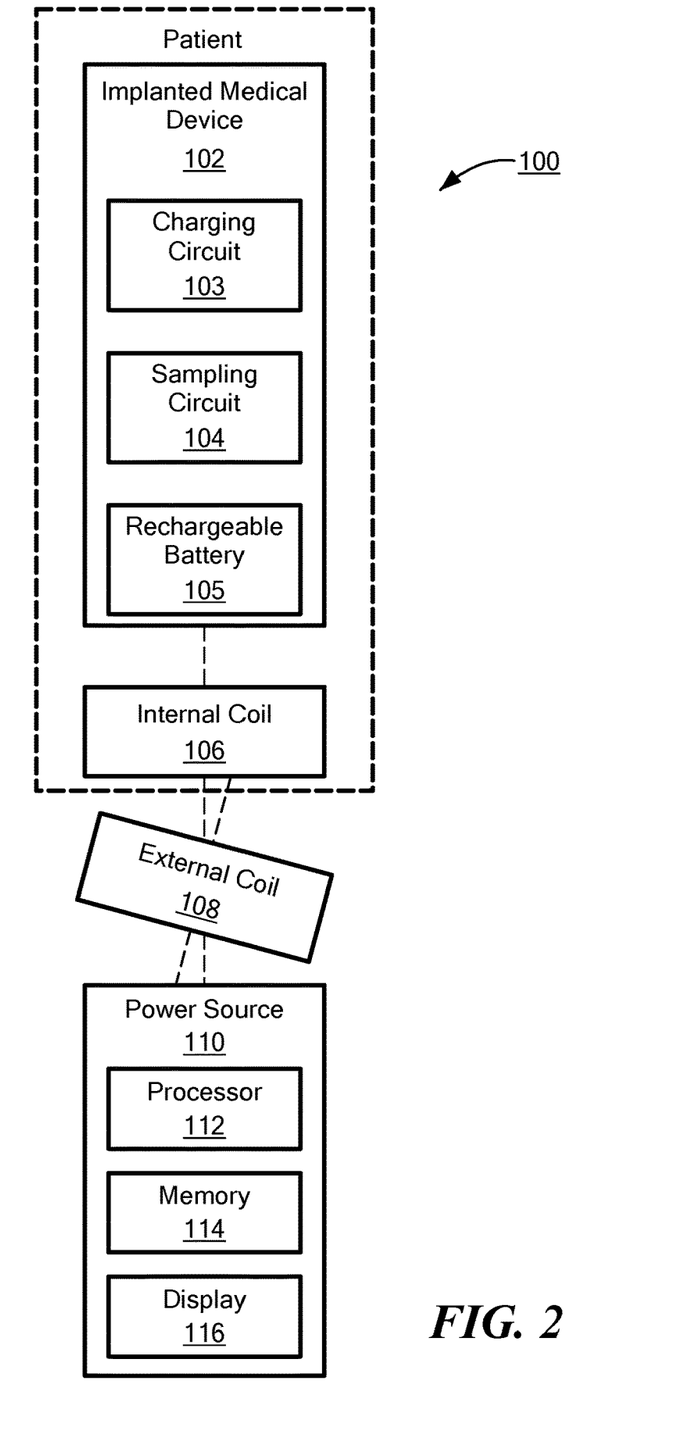
FIG. 2 is a block diagram of a system of charging an implanted medical device implanted in a patient in accordance with principles set forth herein.

Referring now to the drawings in which like reference designators refer to like elements there is shown in FIG. 2 a block diagram of a system 100 of charging an implanted medical device 102, implanted in a patient and having a charging circuit 103, a sampling circuit 104, a rechargeable battery 105 and an internal coil 106, the internal coil 106 being implanted internal to the patient and not necessarily internal to the implanted medical device 102. The charging circuit 103 receives power from the internal coil 106 and develops a current suitable to charge the rechargeable battery 105. In some embodiments, there is a sampling circuit 104 which samples, directly or indirectly, an amount of power received at the terminals of the internal coil 106, or otherwise samples the received power, and transmits the sampled value to a power source 110. This transmission may be via a wireless transceiver (not shown) or via the internal coil 106 and an external coil 108 coupled to the power source 110.

In FIG. 2, the external coil 108 is shown misaligned with the internal coil 106. Ideally, the internal coil 106 is aligned to the external coil 108 such that an axis of the internal coil 106 coincides with an axis of the external coil 108 and such that the two coils are in proximity. The greater the alignment of the coil axes and the closer the coils are, the greater is the efficiency of power transfer from the external coil 108 to the internal coil 106. Power transfer efficiency depends on the relative orientation of the coils 106, 108. Distances between the coils 106 and 108 may range from a minimum separation of about 4 mm and a maximum separation of 4-5 cm, in some embodiments. The external coil 108 is connectable to the power source 110 which has power, either onboard, received wirelessly or received by a cable from a more powerful power source such as, for example, an electrical outlet providing 110-volt AC power. Thus, in some embodiments, the power source 110 may itself be a rechargeable device. The power source 110 may include a processor 112, a memory 114 and a display 116.

Figure 3:
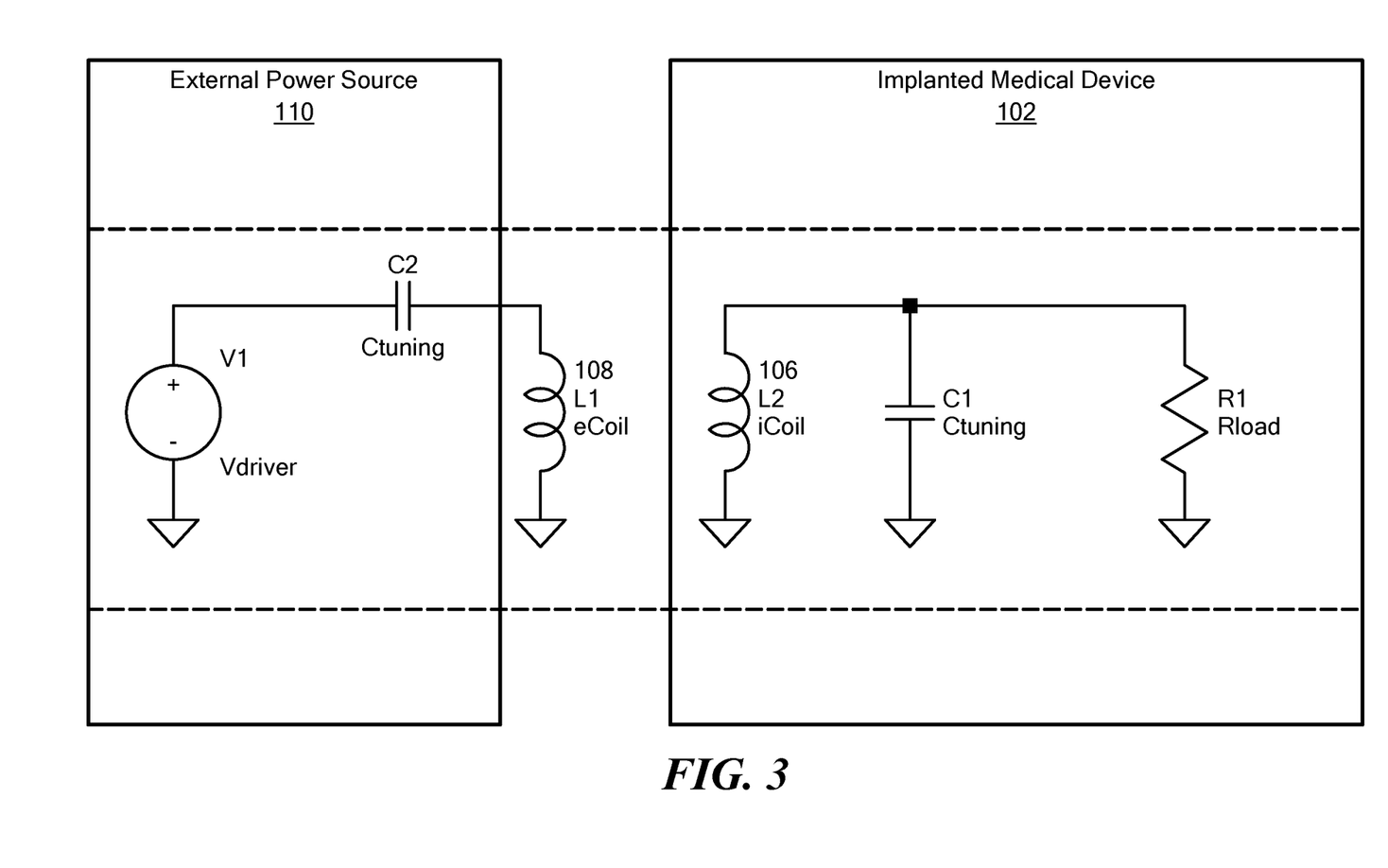
FIG. 3 is an equivalent circuit diagram for one embodiment according to principles set forth herein.

In some embodiments, the processor 112 is configured to determine a coupling coefficient based on a computed efficiency of power transfer or based on a resonance frequency of the system or based on both. In these methods, in some embodiments, a coupling coefficient can be based at least in part on the magnitude of the power received by the internal coil 106. Other measurements to be used to determine coupling efficiency may be used. The system for which the resonance frequency may be determined includes at least the external coil 108 coupled to the internal coil 106 and may include circuitry to which the internal coil is connected. Such a system may be represented schematically in FIG. 3 which shows the external power source having a driving voltage V1 coupled to the external coil L1 (108) via a tuning capacitor C2. The external coil L1 (108) is inductively coupled to the internal coil L2 (106). The internal coil 106 is coupled to circuitry which may include a tuning capacitor C1 and an effective load impedance R1. For example, in some embodiments, the tuning capacitor C1 and load impedance R1 may represent or be equivalent to charging circuitry 103. For example, in some embodiments, the value of C1 may be tuned to change the resonant frequency of the LC circuit formed by L2 and C1. Further, in some embodiments, the load impedance R1 may include a rectifier to convert an alternating current (AC) signal to a direct current (DC) signal suitable to charge the rechargeable battery 105 or power the implanted circuitry and blood pump. The capacitor C2 or a similar set of circuit components may be used to tune the applied operating frequency toward a resonant frequency of the system that includes the two coils, C1, C2 and R1.

Returning now to FIG. 2, the relationship between the coupling coefficient and the efficiency or resonance frequency may be stored as a table in the memory 114. For example, for each of a plurality of efficiencies, a corresponding coupling coefficient may be stored in the memory 114. The memory 114 may include random access memory (RAM) and read only memory (ROM). The efficiency may be, for example, computed by the processor 112 as the ratio of an output power to input power, where the input power is the power applied to the external coil 108 and the output power is the power output from the terminals of the internal coil 106 or may be the power delivered to the load R1. In some embodiment, the power output at the terminals of the internal coil 106 or other indication of power coupled out of the internal coil 106 may be transmitted to the power source 110 from the sampling circuit 104 to enable the processor 112 to compute the efficiency.

Figure 4:
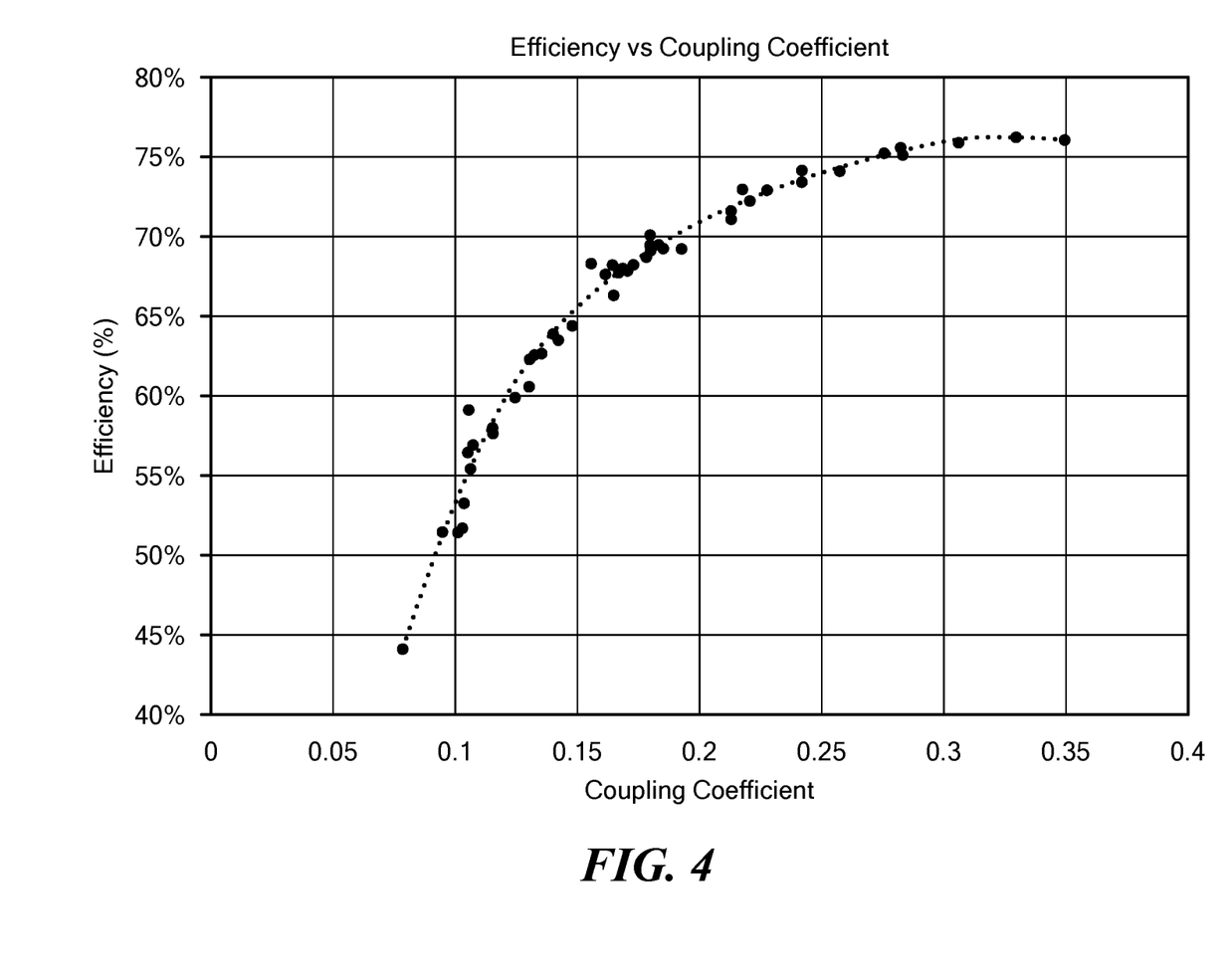
FIG. 4 is a plot of efficiency versus coupling coefficient.

The external power source 110 may be calibrated by predetermining and storing an efficiency for each of a plurality of orientations between the external coil 108 and the internal coil 106. In the alternative to, or in addition to, storing pairs of efficiencies and coupling coefficients in the memory 114, the coupling coefficients may be determined by a formula that relates the determined efficiency to a coupling coefficient. This formula may be derived by, for example, a polynomial approximation of a curve that best fits data points (x=coupling coefficient, y=efficiency), obtained from calibration of the system that includes the external coil 108, the internal coil 106 and circuitry to which the internal coil is coupled, which may include the charging circuitry 103. One example of such a curve and data points is shown in FIG. 4, where efficiency versus coupling coefficient is shown with data points and an approximating curve.

The indication of output power obtained by the sampling circuit 104 may be transferred to the external power source via the coupling between the internal coil 106 and the external coil 108. Alternatively, the indication of output power obtained by the sampling circuit may be transferred to the external power source wirelessly via a wireless transmitter (not shown) of the implantable medical device 102.

Figure 5:
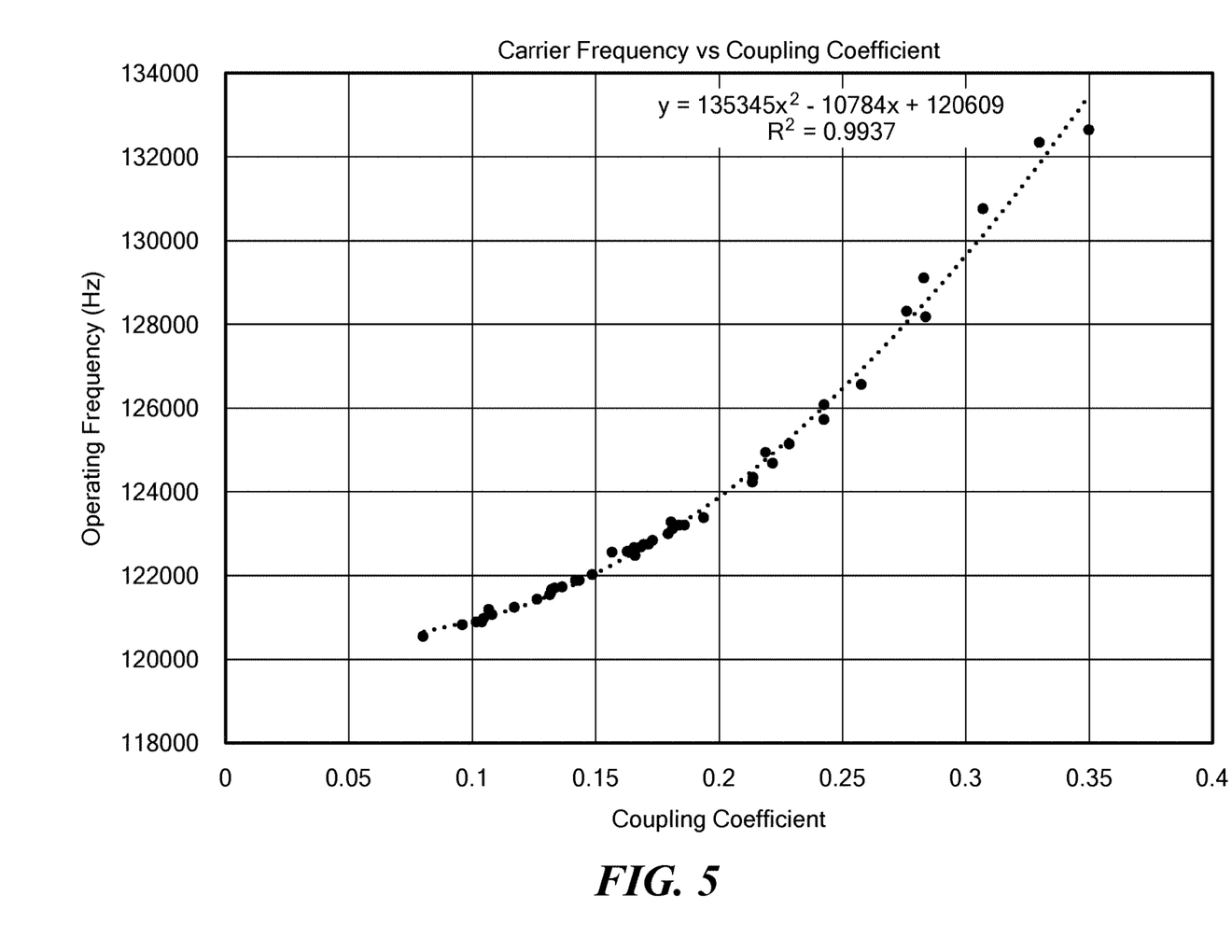
FIG. 5 is a plot of operating frequency versus coupling coefficient.

In some embodiments, the memory 114 may be configured to store, for each of a plurality of operating frequencies, a corresponding coupling coefficient, where each operating frequency approaches a resonant frequency exhibited by the system that includes: the external coil 108, the internal coil 106 and circuitry to which the internal coil is coupled, which may include the charging circuitry 103. The external power source 110 may be calibrated by predetermining an operating frequency that approaches resonance for each of a plurality of orientations between the external coil 108 and the internal coil 106. In the alternative to, or in addition to, storing pairs of operating frequencies and coupling coefficients in the memory 114, the coupling coefficients may be determined by a formula that relates the determined operating frequency to a coupling coefficient. This formula may be derived by, for example, a polynomial approximation of a curve that best fits data points (x=coupling coefficient, y=operating frequency) obtained from calibration of the system. One example of such a curve and data points is shown in FIG. 5, where efficiency versus operating frequency is shown with data points and an approximating curve.

Note that the term, coupling coefficient, may imply a coefficient that if multiplied by power in the external coil, would produce a corresponding power in the internal coil. Other definitions of coupling coefficient may be employed, so that in the general sense, the coupling coefficient may be a number whose magnitude is proportional to an extent of alignment and proximity of the external coil in relation to the internal coil.

A value of the determined coupling coefficient may be displayed by display 116 or, a number, letter, color or other surrogate for the magnitude of the determined coupling coefficient may be displayed by display 116. Display 116 may be a light emitting diode (LED), a liquid crystal display (LCD) or other type of display that can be controlled by electronic circuitry such as the processor 112. In some embodiments, for example, the determined coupling may be displayed on a scale from zero to ten. Or a variable indicator such as a bar may be displayed with a length that is proportional to the coupling coefficient, for example, so that as the external coil 108 becomes more aligned with and/or becomes closer to the internal coil 106, the length of the bar increases. As another example, the angle between the two coils may be displayed as two intersecting or parallel lines according to the alignment between the two coils. Thus, as the patient using the external power source 110 rotates the external coil such that the external coil axis tilts relative to the internal coil axis, the display 116 may display a changing real-time indication of the change in relative orientation of and/or the distance between the coils.

In the alternative to, or in addition to, display 16, an audio device may be employed that emits an audible tone or other audible signal when there is coupling, the tone or other audible signal increasing in frequency or tempo as the coupling gets stronger, for example. As an example, a tone may be pulsed with increasing pulse rate as a function of coupling strength.

In some embodiments, the processor 112 may be a microcontroller or microprocessor that can be programmed to execute instructions to perform at least some of the functions herein attributable to the power source 110. For example, an algorithm for determining and causing display of an indication of alignment (such as the determined coupling coefficient, or the bar display, or the intersecting lines or other surrogate indication of alignment), may be programmed by computer instructions that cause the processor to compute an efficiency and look up a corresponding coupling coefficient in a table. As another example, the algorithm may be implemented by computer instructions that cause the processor to change a frequency applied to the external coil 108, to determine a coupling coefficient based on the applied (operating) frequency, and to display an indication of alignment.

Note that in some embodiments, a device that is physically separated from the external power source and the implantable medical device may be configured to generate the indication of alignment. The physically separated device may be in wireless or wireline communication with at least one of the external power source and the implantable medical device, and may be a cell phone, wrist worn device, tablet, or other device having at least one of a speaker and a display to make the indication of an extent of inductive coupling between the coils. In addition to making the indication, the separate device may perform computations of a coupling coefficient as well as other computations incidental to generating the indication of an extent of coupling.

Figure 6:
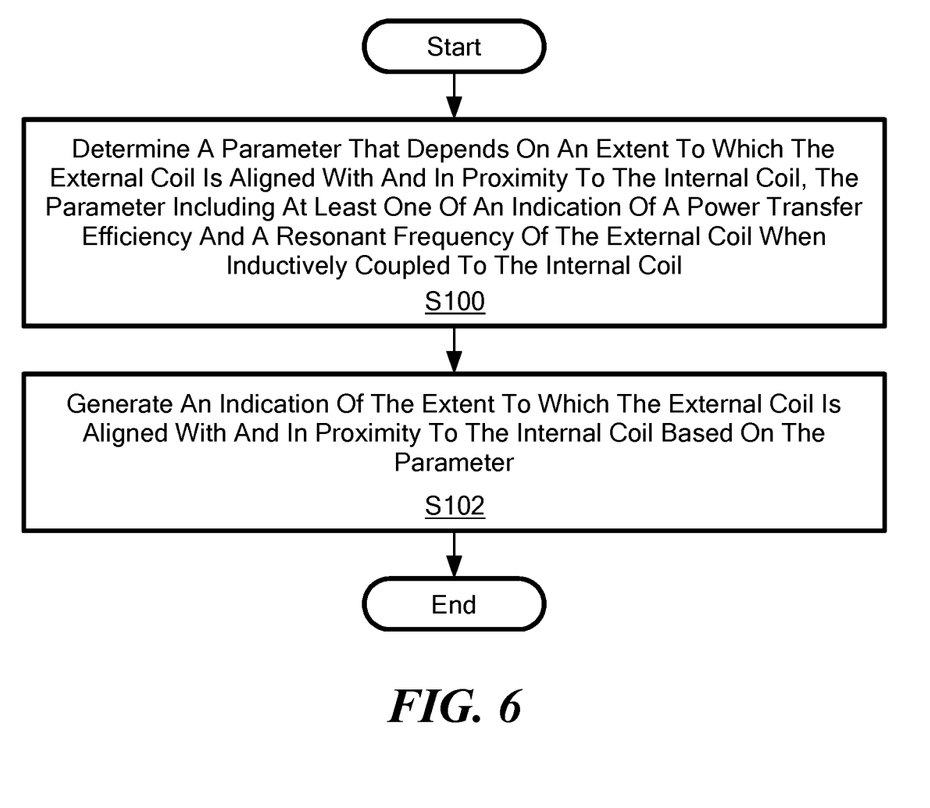
FIG. 6 is a flowchart of an exemplary process for indicating an extent to which an external coil is aligned with and in proximity to an internal coil according to principles set forth herein.

FIG. 6 is a flowchart of an exemplary process for providing an indication of coil alignment to a patient having an implanted medical device with a coil internal to the patient through which a rechargeable battery can be recharged from power coupled to the internal coil from external coil coupled to a power source. The process may be performed by the processor 112, memory 114 and display 116. The process includes determining a parameter that depends on an extent to which the external coil is aligned with and in proximity to the internal coil, where the parameter includes at least one of an indication of an internal coil output power and a resonant frequency of the external coil when inductively coupled to the internal coil (Block S100). The process also includes displaying an indication of the extent to which the external coil is aligned with and in proximity to the internal coil based on the parameter (Block S102).

In some embodiments, the display may be of a variable graphical indicator, such as a bar chart or pie chart, for example, with a shaded area representing a strength of coupling between the two coils. For example, a length of a shaded bar on a bar chart may be proportional to a magnitude of the coupling coefficient. In some embodiments, the display may be of two sets of coordinate axes, one set of coordinate axes representing the position and orientation of the external coil 108 and the other set of coordinate axes representing the relative position and orientation of the internal coil 106, so that the relative position and orientation between the two coils can be seen by the patient looking at the display.

Note that some embodiments, may indicate an extent of alignment based on more than one factor and may be based on at least one of an external coil input power, an internal coil output power, an efficiency and/or a resonant frequency as discussed above.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An external power source configured to supply power through inductive coupling of power from an external coil to an internal coil associated with an implanted medical device, the external power source comprising:
 a memory;
 a processor in communication with the memory, the processor configured to:

receive an internal coil output power;

determine an efficiency as a ratio of the internal coil output power to an amount of power applied to the external coil;

track a resonant frequency of the external coil based on adjustments to a driving frequency applied to the external coil;

determine a coupling coefficient based on the efficiency and the resonant frequency; and generate an indication of an orientation of the external coil relative to the internal coil, the indication based at least in part on the coupling coefficient.

2. The external power source of claim 1, wherein the indication of orientation is an audible tone that changes in frequency as the orientation changes.

3. The external power source of claim 1, wherein the processor is further configured to determine the coupling coefficient based on a look up table stored in the memory, the look up table providing a different coupling coefficient for each of a plurality of efficiency values and received power values.

4. The external power source of claim 1, wherein the processor is further configured to determine the coupling coefficient is according to a formula that relates the efficiency to the coupling coefficient.

5. The external power source of claim 1, wherein the indication includes a variable graphical indicator that varies according to an alignment of the external coil relative to the internal coil.

6. The external power source of claim 1, wherein the indication varies as an angle between an axis of the external coil and an axis of the internal coil varies.

7. The external power source of claim 1, wherein the indication varies as a distance between the external coil and the internal coil varies.

8. The external power source of claim 1, wherein the external power source is configured to adjust a driving voltage via a tuning capacitor to adjust the driving frequency.

9. A method for indicating an extent of inductive coupling of power from an external coil to an internal coil associated with an implanted medical device, the method comprising:

determining an efficiency as a ratio of an internal coil output power to an amount of power applied to the external coil;

tracking a resonant frequency of the external coil when inductively coupled to the internal coil based on adjustments to a driving frequency applied to the external coil;

determining a coupling coefficient that indicates an extent to which the external coil is aligned with and in proximity to the internal coil, the coupling coefficient being based at least in part on the efficiency and the resonant frequency of the external coil; and generating an indication of the extent to which the external coil is aligned with and in proximity to the internal coil based on the coupling coefficient.

10. The method of claim 9, wherein the indication is an audible tone that varies in frequency as an orientation of the external coil varies with respect to an orientation of the internal coil.

11. The method of claim 9, wherein at least one of a cell phone or a wrist worn device in wireless communication with at least one of an external power supply having the external coil and the implanted medical device communicates the indication.

12. The method of claim 9, further comprising adjusting a driving voltage via a tuning capacitor to adjust the driving frequency.

* * * * *